United States Patent [19]

Gramont

[11] Patent Number: 4,579,456

[45] Date of Patent: Apr. 1, 1986

[54] PROCESS AND DEVICE FOR THE QUANTITY DETERMINATION OF SMALL AMOUNTS OF GASEOUS COMPONENTS IN A GAS MIXTURE

[75] Inventor: Louis Gramont, Champlan, France

[73] Assignee: Office National d'Etudes et de Recherches, Chatillon Sous Bagneux, France

[21] Appl. No.: 519,929

[22] Filed: Aug. 3, 1983

[30] Foreign Application Priority Data

Aug. 3, 1982 [FR] France .............. 82 13551

[51] Int. Cl.⁴ ............................... G01N 21/61
[52] U.S. Cl. .................... 356/409; 250/345;
250/351; 250/338; 350/274; 350/275; 356/414
[58] Field of Search .............. 250/343, 345, 351, 373,
250/338 GA; 350/273, 274, 275; 356/51, 409,
414, 416, 432, 433, 434, 436, 437, 438, 439

[56] References Cited

U.S. PATENT DOCUMENTS

| | | | |
|---|---|---|---|
| 3,038,083 | 6/1962 | Lunzer | 350/275 |
| 3,049,962 | 8/1962 | Denecke | 350/275 |
| 3,279,308 | 10/1966 | Bartz et al. | 356/51 |
| 3,790,289 | 2/1974 | Schmidt | 356/434 |
| 3,790,798 | 2/1974 | Sternberg et al. | 356/51 |
| 3,811,776 | 5/1974 | Blau, Jr. | 356/433 |
| 3,869,613 | 3/1975 | Link et al. | 250/343 |
| 3,976,883 | 8/1976 | Krakow | 250/343 |
| 3,976,884 | 8/1976 | Acton et al. | 250/343 |
| 4,004,146 | 1/1977 | Blunck | 356/51 |
| 4,193,695 | 3/1980 | Kojima et al. | 350/275 |
| 4,288,693 | 9/1981 | Fabinski et al. | 250/345 |

FOREIGN PATENT DOCUMENTS

| | | | |
|---|---|---|---|
| 1208180 | 12/1965 | Fed. Rep. of Germany | 350/275 |
| 847440 | 9/1960 | United Kingdom | 350/273 |

OTHER PUBLICATIONS

"Non-Dispersive Infra-Red Gas Analyzers," Turnbull, M. S., *Electronics and Instrumentation*, V. 2, N. 12, Mar. 1972, pp. 11–15.

"Infra-Red Instrumentation and Techniques," Williams, V. Z., *The Review of Scientific Instruments*, V. 19, N. 3, Mar. 1948, p. 135.

*Primary Examiner*—F. L. Evans
*Assistant Examiner*—Joel L. Harringa
*Attorney, Agent, or Firm*—Larson and Taylor

[57] ABSTRACT

A radiation beam, having passed through the mixture containing the component whose spectral composition contains at least one characteristic spectral line of the component, is caused to pass alternately along two channels one of which comprises a definite amount of the gaseous component and the other of which serves as reference. The second channel over which the radiation beam travels is limited to a diaphragm having a radiation transmission substantially equal to that of the first channel in the absence of said component in the mixture. The output beam from the two channels is directed towards a detector for detecting the variation of intensity of the beam through a filter for selecting said characteristic radiation.

5 Claims, 9 Drawing Figures

PROCESS AND DEVICE FOR THE QUANTITY DETERMINATION OF SMALL AMOUNTS OF GASEOUS COMPONENTS IN A GAS MIXTURE

BACKGROUND AND SUMMARY OF THE INVENTION

The present invention relates to the quantity determination of a component present in a small amount in a gaseous mixture by absorption of a radiation which is indicative of said component. The term "gaseous" must be interpreted in the widest sense as designating not only a gas properly speaking but also a vapor or a dispersion.

Numerous processes are already known for determining the quantity of a component present in a small amount in a gaseous mixture. Processes in particular are known of the type in which a radiation beam having passed through the mixture and whose spectral composition contains at least one spectral absorption line characteristic of the component alternately traverses two channels one of which comprises a given amount of the gaseous mixture and the other of which serves as reference.

It is an object of the invention to provide an improved process and device of that type. It is a more specific object to provide a device which is simple in construction and however of high sensitivity. It is still another object to provide a simple solution to the problem of selectivity of the measurement in the case where absorption spectral lines belonging to parasite gases are superimposed on those of the gaseous component whose amount has to be determined. Finally, in a particular embodiment, it is an object of the invention to eliminate the influence of a possible polarization of the light beam which is passed through the mixture.

To this end, a process of the above-defined kind according to the invention includes the step of constituting the second channel over which the radiation beam travels as a diaphragm having a radiation transmission substantially equal to that of the first channel in the absence of said component in the mixture. The output beam from the two channels is fed to a detector detecting the intensity variations of the beam, through a filter selecting said characteristic radiation.

The invention proposes also a device for the quantity determination of a component present in a small amount in a gaseous mixture, comrising means for directing alternately a radiation beam containing at least one spectral absorption line which is characteristic of the component, along a first channel which comprises a volume of said component and a second channel comprising a diaphragm calibrated so as to have a transmission substantially equal to that of the first channel when the mixture does not contain said component, as well as means for directing the beams coming from the two channels, through a filter transmitting a given fraction of the spectral absorption band of the component to be detected, towards a detector associated with means for measuring the variations of the output signal of the detector.

To increase selectivity, when the mixture is likely to contain a small amount of parasite gas, a given amount of the parasite gas, greater than that likely to be passed through by the beam in the second channel, may be interposed in the optical path common to the two channels.

The incident radiation beam may be formed by natural light. A light source will very often be used adapted to the spectral range of the characteristic radiation, which may, depending on the case, be in the ultra-violet, the visible or the infrared, (this latter case excluding the use of natural light). In the case of measuring the concentration of gas in the atmosphere, the above-defined elements may be combined together in the same apparatus, but the emission of the source through the atmospheric zone where the measurement takes place is then reflected by a directive reflector placed at a distance, for example by a catadiopter which removes the problems of aiming the reflector.

The invention will be better understood from reading the following description of particular embodiments given by way of non limiting examples.

SHORT DESCRIPTION OF THE DRAWINGS

Figure 2:
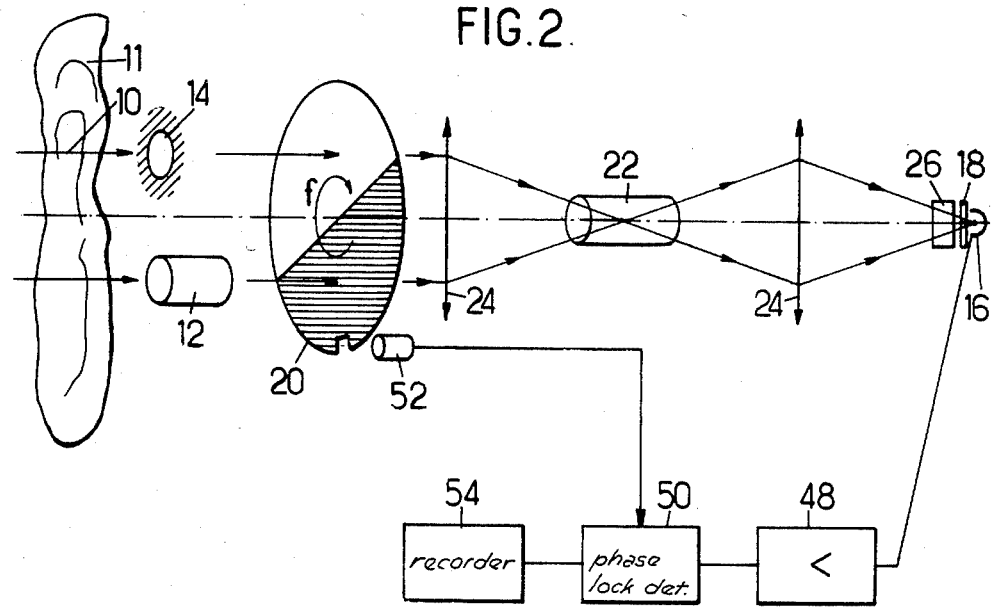
FIG. 2 is a simplified diagram of a device according to a first embodiment of the invention, using a rotary flap for alternately orientating the beam towards two transmission channels.
Figure 3:
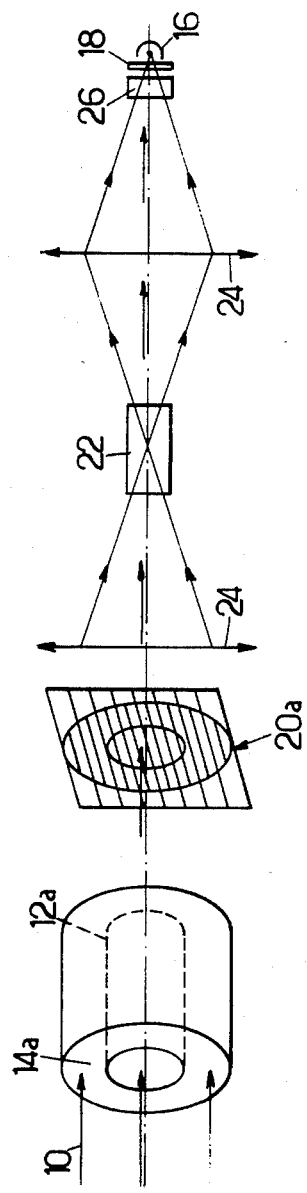

FIG. 3, similar to FIG. 2, shows another embodiment of the invention, using an annular opening surrounding the tank.

FIG. 4 shows schematically one possible construction of the means for orientating the beam of the device of FIG. 3.

Figure 5A:
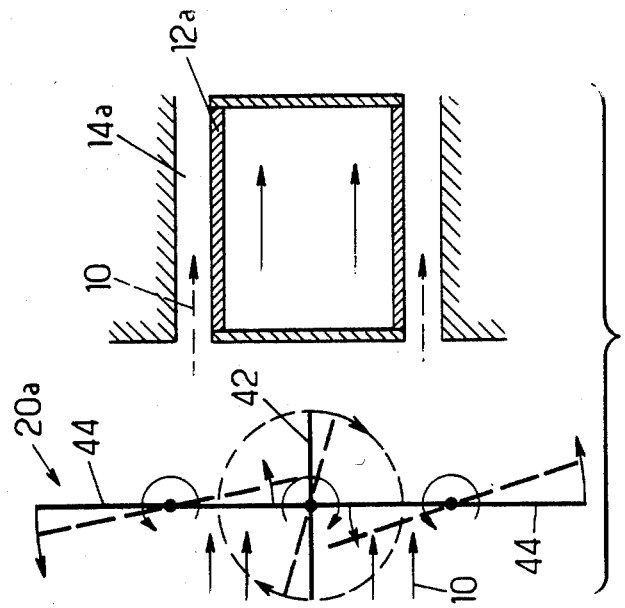
Figure 5B:
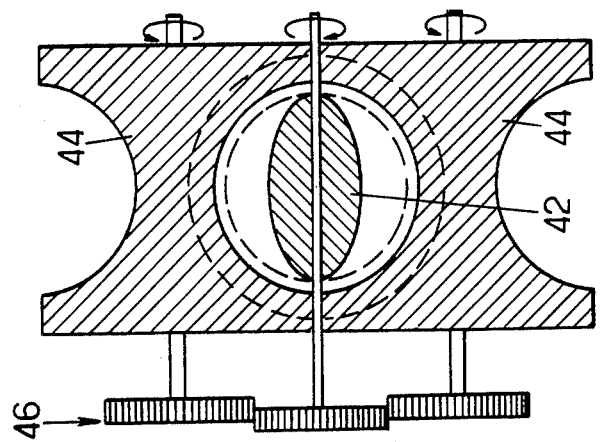

FIGS. 5A and 5B show, respectively in a front view and a side view a variation of the means for orientating the beam of FIG. 3.

Figure 6:
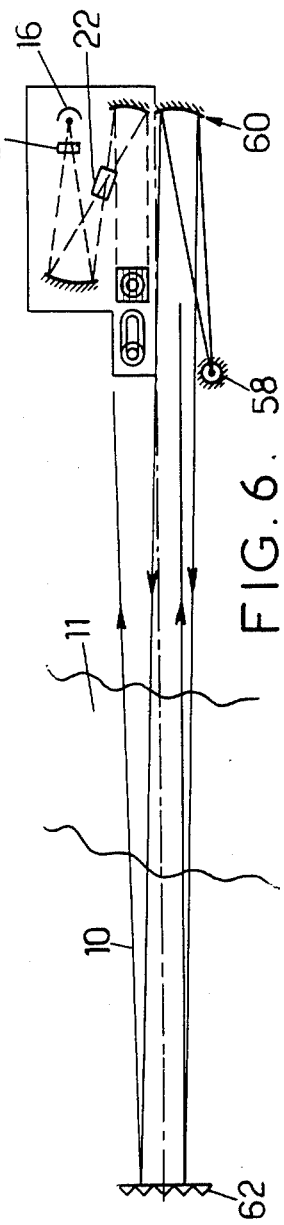

FIG. 6 shows a possible arrangement of the device for detecting and determining the quantity of the gas in the atmosphere.

DETAILED DESCRIPTION OF THE PREFERRED EMBODIMENTS

In its principle, the process of the invention uses the modulation of the signals supplied by an electro-optical detector which receives a light beam which has passed through the mixture containing a component whose quantity is to be determined, alternately along two channels.

In one of the channels the beam, which has already undergone attenuation resulting in a transmission coefficient $\tau(u_1)$ passing through the mixture, passes through a diaphragm which limits the section of the beam, which results in a transmission coefficient k. In the other channel, the same beam passes through a tank containing a well-defined amount of the gas whose quantity is to be determined, possibly mixed with another gas not having an absorption band covering that of the gaseous component to be detected. This tank has a transmission coefficient $\tau(u_2)$ dependent on the amount $u_2$ of gas which it contains.

Figure 1A:
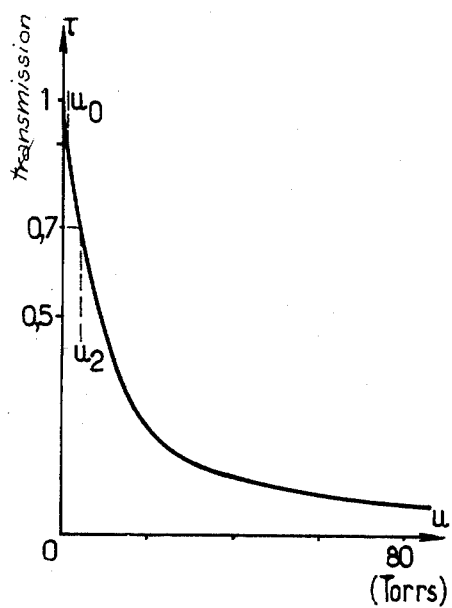
FIGS. 1A and 1B are curves representative of the variation of the transmission $\tau$ of a mixture depending on the proportion u (expressed as a partial pressure) of $NO_2$ and $C_2H_4$ respectively, for 450 nm and 3.3 $\mu$m radiations.
Figure 1B:
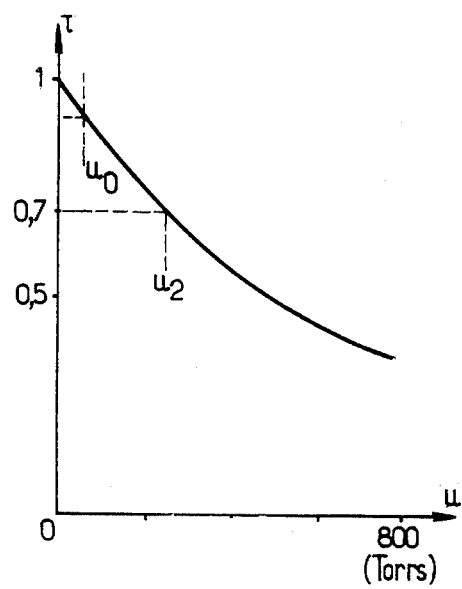

The curve representative of the transmission $\tau$ as a function of the amount of component whose quantity is to be determined through which the beam passes has the trend shown in FIG. 1A or 1B. In these curves, the amount of gaseous compound absorbing the radiation is indicated by its pressure, (possibliy its partial pressure) in the tank, of given volume.

The beams leaving the diaphragm and the tank are alternately fed to the detector, preceded by a filter centered on the absorption band of the gaseous component whose quantity is to be determined. The spectral composition of the beam which passes through the mixture to be studied, then travels over one or other of the two channels towards the detector, is chosen as a function of the spectral absorbtion band.

It is arranged for the transmission by the calibrated diaphragm in the spectral range defined by the filter to be the same as that of the tank, so that we have, at equilibrium:

$$k = \tau(u_2).$$

In this case, a modulation of the signal appears when an amount of gas ($u_1$) is present in the optical path upstream of the two channels. The amplitude of this modulation is proportional to the amount of gas $u_1$ passed through and it depends moreover on the derivative $d\tau/du$ measured for the values $u_0$ and $u_2$. The value $u_0$ is the mininum amount for which it is possible to measure the derivative, as will be explained later. In FIGS. 1A and 1B, $u_2$ has been chosen to correspond to a transmission coefficient of 70%.

The modulation rate obtained will be:

$$\left(\frac{d\tau}{du}\right)_{u_0} k - \left(\frac{d\tau}{du}\right)_{u_2} \quad (1)$$

In this formula $(d\tau/du)_{u_0}$ designates the slope of the variation curve at the origin of the curve, i.e. for a transmission coefficient equal to 1. As it is not possible in practice to measure the slope at this point, it is measured close by. For example, in FIGS. 1A and 1B, the measurement of the slope is effected for a value of $u_o$ which corresponds to a transmission coefficient between 0.9 and 1.

To implement the process, the device shown in FIG. 2 may be used. This device comprises advantageously an artificial radiation source, not shown. The incident beam 10, formed by the light coming from the source, passes through zone 11 in which is present the component whose quantity is to be determined. The device comprises two parallel channels. The first one is formed by a sealed tank 12, tubular in shape, closed by covers transparent to the radiation used for the measurement. Tank 12 contains an amount of the gaseous component to be detected at 11 chosen so that its transmission coefficient is between 0.5 and 0.7. The length of the tank will depend naturally on the mean intensity of the absorption and the pressure in the tank may be brought to a value close to the atmospheric pressure by addition of a gas not having an absorption band overlapping the band in which the measurement takes place, for example by means of dry nitrogen.

The other channel is formed by a circular diaphragm 14, of a transmission coefficient k, whose axis is parallel to that of the tube.

Means placed upstream or downstream of tank 12 and of diaphragm 14 allow a detector 16 to receive alternately, through a filter 18, the light travelling along one or the other of the two channels. These means are formed by an optical half-moon modulator 20 driven with a rotational movement at a constant speed about its axis, as shown by arrow f. When it rotates, this modulator alternately shuts off the two channels and lets the incident radiation pass progressively from one channel to the other.

The device shown in FIG. 2 further comprises a tank 22 and an optical system (lenses 24 or mirrors) letting pass the whole of the light coming from one and the other of the channels through the tank. This latter is intended to receive a well-defined amount of the parasite gases likely to be present in zone 11 at the same time as the gas whose quantity is to be measured. This tank, providing identical absorption in both channels, considerably increases the selectivity of the measurement by limiting the effects of a variation of the parasite gas content in zone 11.

The device may also comprise a calibrating system formed by a turret carrying several small tanks 26, in the vicinity of detector 16. By rotating the turret, these tanks which contain known and different amounts of the gas to be detected and whose quantity is to be determined, are brought successively over the common optical path and thus to calibrate the device. One of the tanks is empty so that the zero can be adjusted while compensating for losses due to the absorption by the covers. A small size adjustable flap also allows the values of the transmissions over the two channels to be equalized.

The device of FIG. 2 has the disadvantage of being sensitive to the possible polarization of the light, when this comes from the sky. This defect may be substantially attenuated by placing in the two channels, before the input lens 24, a polarizing plate, transparent in the spectral range used. But this disadvantage is removed in the embodiment shown in FIG. 3 where the diaphragm 14a is formed by an annular opening, defined by a tube concentric with the tank 12a containing a predetermined amount of the component to be detected. This tube may also be used as sunshade by extending it outwardly. The other elements of FIG. 2 are to found again in FIG. 3.

In the case of FIG. 3, a half-moon optical modulator of the kind shown in FIG. 2 can no longer be used. FIGS. 4 and 5 show two variants adaptable to the case of an annular diaphragm.

Figure 4B:
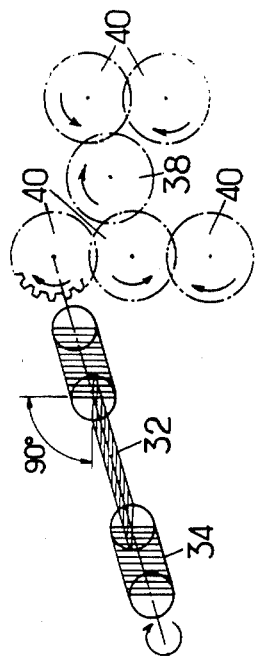
Figure 4A:
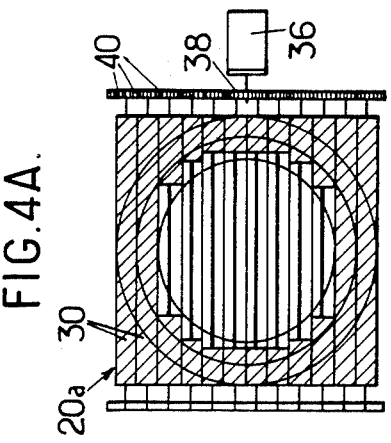

Modulator 20a shown in FIGS. 4A and 4B comprises a curtain of blades 30 rotating about parallel axes. The first and last two blades (in the vertical direction) are entirely located in the first channel. They are consequently in a single section. On the contrary, the intermediate blades, for example the four middle blades one of which is shown in FIG. 4B, have a central section 32 and two lateral sections 34, at 90° from section 32 so that the beam directed towards the tank is completely stopped when the beam which passes through the diaphragm is free and conversely. It can be seen that the radiation arrives alternately through the tank and through the diaphragm. Any appropriate means may be used for driving all the blades in synchronism. For example, a motor 36 may be coupled to a central gear 38 which controls two gear trains 40 each associated with a blade.

A simpler solution than that of FIGS. 4A and 4B, but requiring on the other hand more space, is shown in FIG. 5. In this figure, where the parts corresponding to those already shown in FIG. 3 bear the same reference number, the means for alternately orientating the radiation through tank 12a and through the diaphragm 14a are formed by a central disk 42 rotating about an axis perpendicular to that of the tank, and two external plates 44 rotating about axes parallel to the preceding one. The central opaque disk has an area equal to the effective area of the input cover of tank 12a. It is rotated at a constant speed by a motor not shown. The two external plates 44 are synchronized in rotation with the central disk 42, for example by means of a gear train 46, and are situated in the same plane when disk 42 has its edge to the incident radiation. Plates 44 are cut out so as to interrupt completely the passage of a beam through diaphragm 14a and to free completely the passage of the radiation towards tank 12a when they are in the same plane, as shown in FIG 5B.

The device is completed by a circuit for measuring the output signal modulation of detector 16. This circuit may be similar to the one described in French Pat. No. 2 181 203; such a circuit is shown schematically in FIG. 2. In comprises an amplifier 48 with a pass-band compatible with the frequency set by the means for alternately orientating the radiation (modular disk 20 in FIG. 2). Amplifier 48 drives a synchronous detector 50 which receives a reference signal, for example from a sensor 52 associated with the disk 20. This output signal of detector 50 may be displayed or fed to a recording means 54, for example for recording on a paper strip.

As has already been mentioned, the radiation source is chosen as a function of the nature of the gas to be measured. It is convenient to use the sky when the measurements may be effected in ultraviolet or visible light and are scheduled solely in daytime. The effect of the polarization and of absorption by clouds, smoke and index variations may be greatly attenuated by using the concentric arrangement shown in FIG. 3.

When, on the contrary, it is desired to work with infrared or at night, it is necessary to use an artificial light source. In near infrared, at about 3 microns, and in visible light, a tungsten filament lamp may in particular be used placed at the focal point of a collimator. In this case, it is convenient to combine the source and the measuring apparatus properly speaking in the same assembly and to place a reflecting device beyond the zone where the component to be detected is to be found. Thus we arrive at the arrangement shown schematically in FIG. 6. The reflecting device will advantageously be a corner reflector so as to remove the problem of orientating the device and of stability in the case of vibration.

In the device shown in FIG. 6, source 58 is associated with a collimating mirror 60 which provides a parallel beam, reflected by reflecting trihedrons 62 at a distance which may be several hundreds of meters. The radiation flux 10, which passes twice through the zone to be studied 11 (which increases the sensitivity) is picked up by the means for alternately orientating the radiation towards one or other of the two channels, then by an optical system, for example catadioptric, for concentration on detector 16.

The device thus constructed allows a high sensitivity to be obtained greater than that of the device described in the prior patent already mentioned, while keeping a high selectivity, more especially when a tank containing a given amount of possible parasite gases is placed in the common path of the beams.

I claim:

1. A device for determining the quantity of a component present in a small amount in a gas mixture, including: means for alternately directing a radiation beam containing a characteristic absorption radiation of the component and having passed through the mixture alternately along a first channel which comprises a tank containing a predetermined amount of said component and along a second channel which comprises a diaphragm defining an annular opening concentric with said tank and so calibrated as to have a transmission for said characteristic radiation substantially equal to that of said first channel when the mixture does not contain said component; means for directing the radiation beam from both channels through filter means transmitting at least a predetermined fraction of the spectral absorption band of the component to be detected; a detector arranged to receive the radiation beam exiting from said filter means; and means associated with said detector for measuring the amplitude of the variations of the output signal of the detector.

2. A device according to claim 1, wherein the amount of said component through which the beam passes in the first channel is such that said first channel has a transmission coefficient between 50 and 70%.

3. The device according to claim 1, characterized in that the means for directing the beam comprise a curtain of blades rotating in synchronism about parallel axes, said curtain having a central part formed by central sections of a part of the blades, which sections are perpendicular to the rest of the blades.

4. The device according to claim 1, characterized in that the means for alternately directing the beam comprise a central disk for interrupting the channel comprising the tank (12a), rotating about an axis transversal to the beam, and two external plates for interrupting the channel comprising the diaphragm, rotating in synchronism with the disk about axes parallel to that of the disk with an offset of 90°.

5. The device according to claim 1 characterized in that it comprises, on a common part of the beam, a tank containing a definite amount of the absorbing parasite gases likely to be met with in the mixture.

* * * * *